United States Patent
Ricky

(10) Patent No.: US 9,636,578 B1
(45) Date of Patent: May 2, 2017

(54) GOLF CLUB SIMULATION APPARATUS

(71) Applicant: Brett Ricky, Overland Park, KS (US)

(72) Inventor: Brett Ricky, Overland Park, KS (US)

( * ) Notice: Subject to any disclaimer, the term of this patent is extended or adjusted under 35 U.S.C. 154(b) by 84 days.

(21) Appl. No.: 14/613,160

(22) Filed: Feb. 3, 2015

Related U.S. Application Data

(60) Provisional application No. 61/935,064, filed on Feb. 3, 2014.

(51) Int. Cl.
| | |
|---|---|
| A63F 13/245 | (2014.01) |
| A63F 13/812 | (2014.01) |
| A63F 13/211 | (2014.01) |
| A63B 15/00 | (2006.01) |
| A63B 21/045 | (2006.01) |
| A63B 49/00 | (2015.01) |

(52) U.S. Cl.
CPC .......... *A63F 13/245* (2014.09); *A63B 21/045* (2013.01); *A63F 13/211* (2014.09); *A63F 13/812* (2014.09); *A63B 15/00* (2013.01); *A63B 49/00* (2013.01)

(58) Field of Classification Search
CPC . A63B 2060/0081; A63B 60/26; A63B 60/54; A63B 49/00; A63B 15/00; A63B 15/005; A63B 21/045; A63F 13/812; A63F 13/211; A63F 13/245
See application file for complete search history.

(56) References Cited

U.S. PATENT DOCUMENTS

| | | | | |
|---|---|---|---|---|
| 4,878,672 A | * | 11/1989 | Lukasiewicz | A63B 60/42 |
| | | | | 473/233 |
| 6,361,451 B1 | * | 3/2002 | Masters | A01K 87/00 |
| | | | | 280/819 |
| 6,648,769 B2 | * | 11/2003 | Lee | A63B 69/3614 |
| | | | | 473/221 |
| 7,226,365 B2 | * | 6/2007 | Qualizza | A63B 60/42 |
| | | | | 137/14 |
| 7,621,859 B2 | * | 11/2009 | Kim | A63B 69/3623 |
| | | | | 473/219 |
| 7,798,910 B2 | * | 9/2010 | Leadbetter | A63B 69/3614 |
| | | | | 473/207 |
| 7,850,536 B1 | * | 12/2010 | Fitzgerald | A63B 69/3614 |
| | | | | 473/220 |
| 2006/0166738 A1 | * | 7/2006 | Eyestone | A63B 15/005 |
| | | | | 463/36 |

(Continued)

Primary Examiner — William H McCullouch, Jr.
Assistant Examiner — Cathy Zhang
(74) Attorney, Agent, or Firm — Dale J. Ream

(57) ABSTRACT

A golf club simulation apparatus includes an elongate shaft housing having opposed lower and upper ends and defining an interior area. A club head member is coupled to the lower end of the shaft housing. A battery is situated in one of the club head member and the shaft housing. An input member configured to receive club selection data is coupled to an outer surface of the shaft housing and electrically connected to the battery. A mass variability assembly is electrically connected to the input member and includes a weight member situated in the shaft housing that is selectively movable therein according to the club selection data. An electronics module having an angular sensing sensor is situated in the club head member. A bend variability assembly is included in the shaft housing for selectively altering a "feel characteristic" of the shaft housing during a swing motion.

18 Claims, 16 Drawing Sheets

(56) References Cited

U.S. PATENT DOCUMENTS

| | | | | |
|---|---|---|---|---|
| 2008/0280692 A1* | 11/2008 | Cage | ............... | A63B 21/00181 |
| | | | | 473/223 |
| 2010/0093458 A1* | 4/2010 | Davenport | ......... | A63B 53/0466 |
| | | | | 473/223 |
| 2012/0289354 A1* | 11/2012 | Cottam | .............. | A63B 69/3658 |
| | | | | 473/223 |
| 2013/0130822 A1* | 5/2013 | Uvena | .................... | A63B 53/00 |
| | | | | 473/282 |
| 2015/0065263 A1* | 3/2015 | Luttrull | ................. | A63B 53/14 |
| | | | | 473/202 |
| 2015/0202505 A1* | 7/2015 | Halpin | .................. | A63B 53/14 |
| | | | | 473/220 |

* cited by examiner

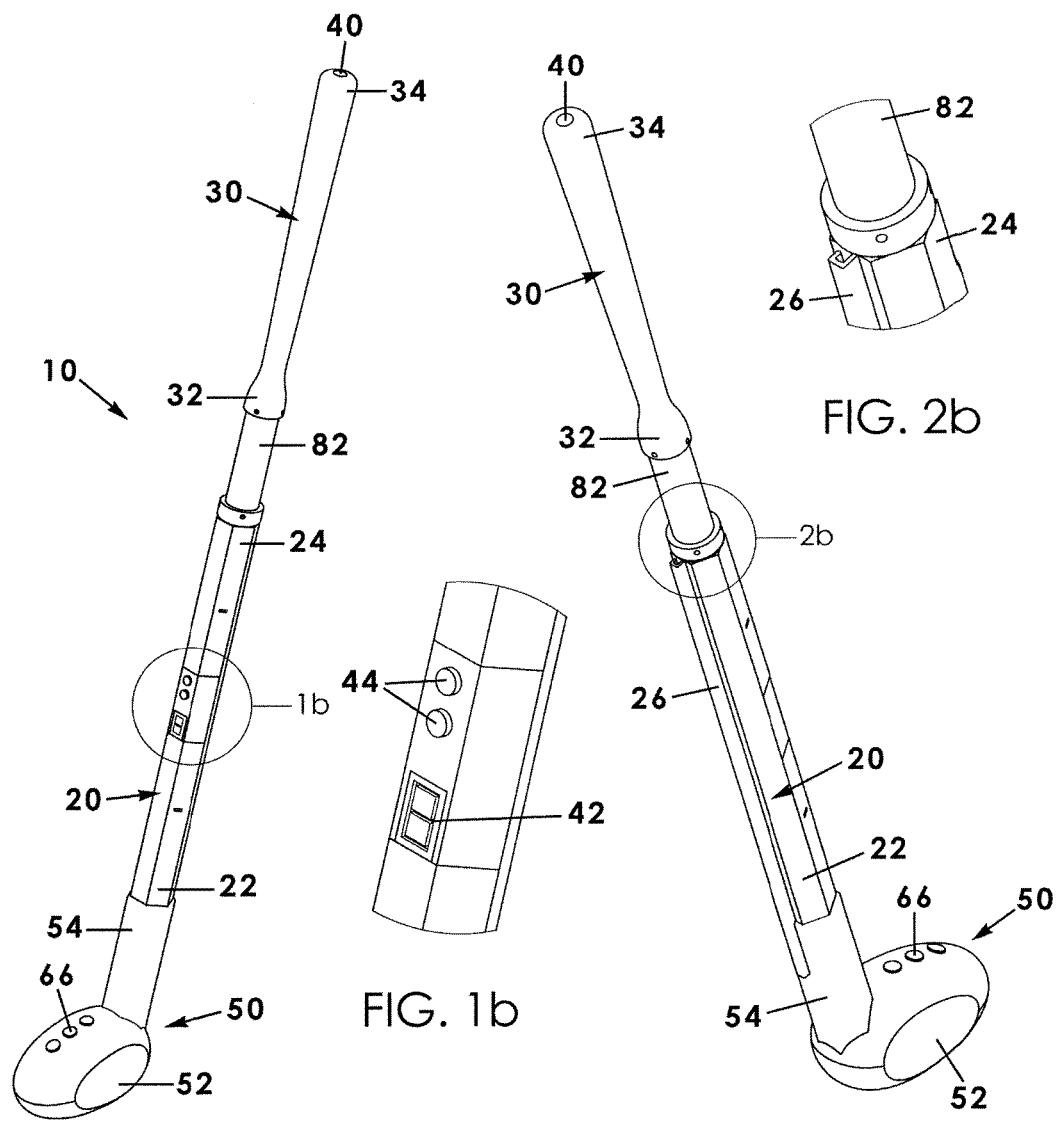

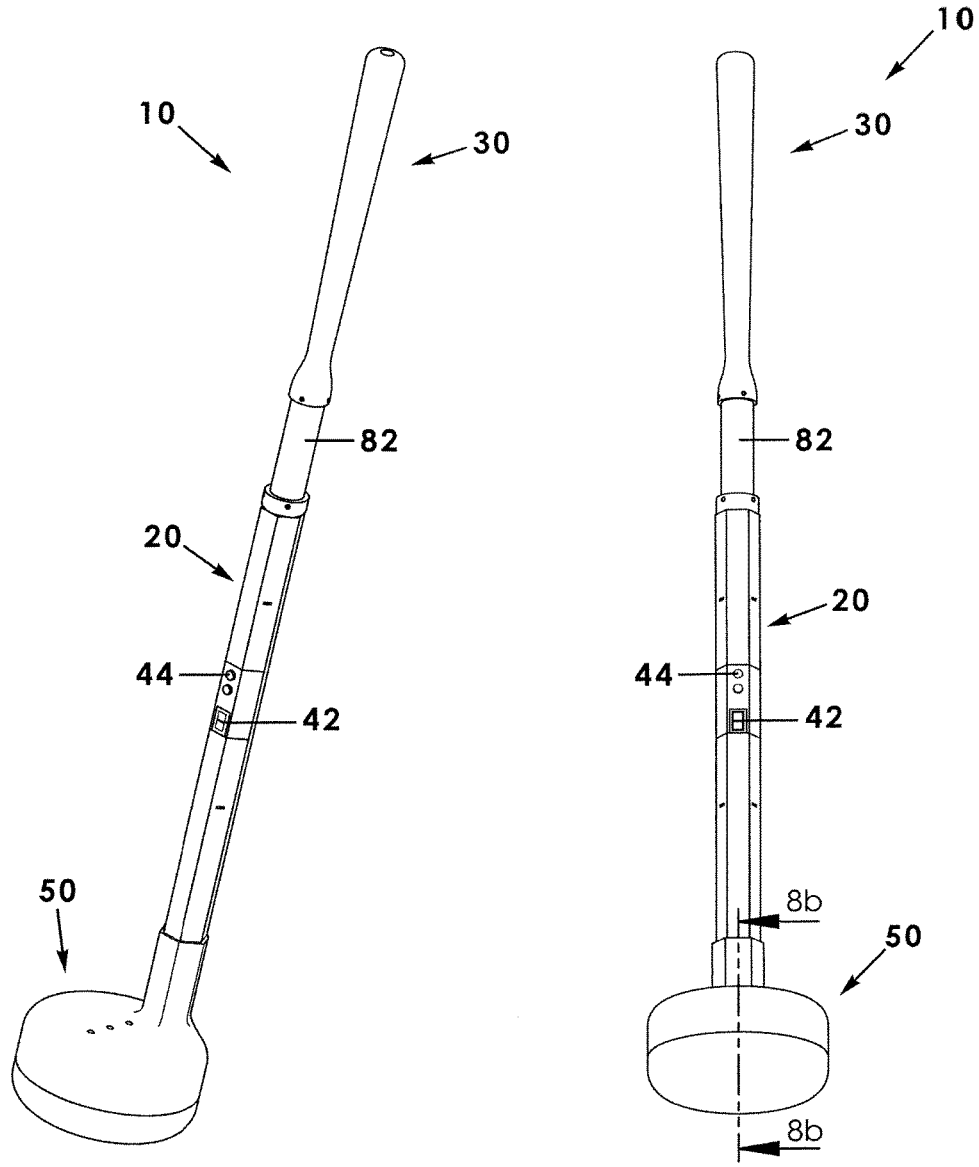

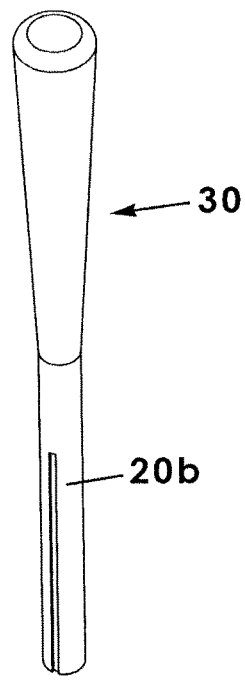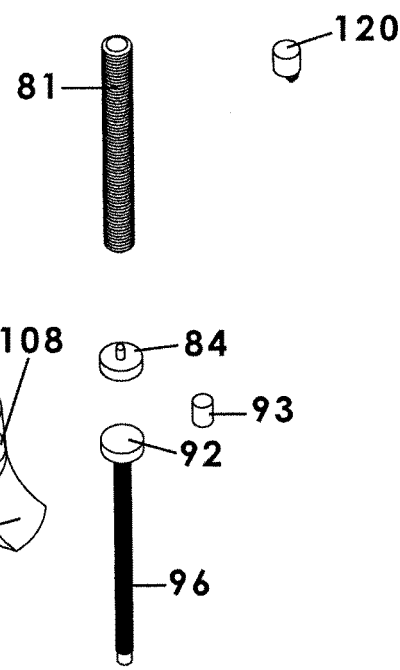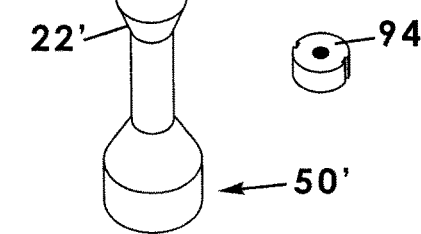
Fig. 11

GOLF CLUB SIMULATION APPARATUS

REFERENCE TO RELATED APPLICATIONS

This application claims the benefit of provisional patent application U.S. Ser. No. 61/935,064 filed Feb. 3, 2014 titled Golf Club Simulation Apparatus.

BACKGROUND OF THE INVENTION

This invention relates generally to sporting goods simulators and, more particularly, to a golf club simulation apparatus that provides a realistic golfing experience using a single miniaturized length golf club. More particularly, the single golf club includes electromechanical assemblies that simulate an entire set of golf clubs.

Although golf is a popular game, the number of people actually playing real golf on a golf course has stagnated in recent years for a number of reasons, including (1) the difficulty of the game without significant practice or game play, and (2) the significant amount of time required for learning proper swing techniques. Simply playing casual video games with traditional interfaces (such as with mouse clicks and joysticks) does not teach realistic swing technique that will encourage gamers to develop actual game skills and then to go out and play the game.

It is well known that a standard set of golf clubs includes clubs having different lengths, weights, grip size, bend characteristics, drag resistance, swing speed, and other parameters. It is very difficult to practice swinging a full set of golf clubs without owning and using a literal full set of clubs in an outdoor environment. It is not feasible to practice with real clubs in an interior environment.

Various golf simulators have attempted to simulate a golf game through computer software and even using a hand-held device in the nature of a wand. Although assumably effective for their intended purposes, the existing devices focus on the visual representations of respective golf courses, hypothetical wind and geographic conditions, and timing of swinging a simulated golf club. The existing golf simulation products do not enable a user to feel and experience the actual length, weight, swing speed/resistance, and impact of actually striking a golf ball. For instance, casual video games, such as on smart phones, online games, and console games, are not effective to teach real golf game skills or to encourage gamers to actually play the game with real golf clubs. Conversely, golf swing training devices require the use of real clubs along with optic technologies including cameras.

The market for sports related video gaming systems is enormous—including an estimated 100 million gamers. Therefore, it would be desirable to have a simulation apparatus and system that actually influences gamers to actually try a sport and train the user regarding the skills and techniques of the sport. Specifically, it would be desirable to have a golf club simulation apparatus that combines the thrill of sports simulation with the physical experience of actually swinging a real golf club. Further, it would be desirable to have a golf club simulation apparatus that is able to change its weight distribution and shaft flexibility/bend so as to simulate the actual feel of selected clubs. In addition, it would be desirable to have a golf club simulation apparatus that trains a user the proper angle of shaft orientation for each of a selectable number of clubs while using only a fixed length club (or a limited variable length club) which allows for swinging indoors without ceiling height restrictions.

SUMMARY OF THE INVENTION

A golf club simulation apparatus according to the present invention has a goal of changing the way people interact with casual games on mobile devices, console games, and the like, and to influence gamers to actually engage in a sport. Specifically, an object of this invention is to "Turn Gamers into Golfers". The apparatus according to the present invention is intended to replace traditional video game controllers such as joy sticks with minor haptic responses (vibration or sound), a computer mouse, mobile touch screen interfaces, and even cameras such as the Wii™. Existing game interfaces do not have a realistic feel interactive interface.

The present apparatus allows for home use so that beginners can play a little and come back often without having to have dedicated travel and golf driving range humiliation. In addition, the avid golfers in the US (about 6.2 million) can use the present apparatus inside and outside and the feedback will allow them to make swing changes, practice and improve.

Specifically, a golf club simulation apparatus according to the present invention includes an elongate shaft housing having opposed lower and upper ends and defining an interior area therebetween. The apparatus includes an elongate grip member having a proximal end operatively coupled to the upper end of the shaft housing and a distal end opposite the proximal end, the grip member defining an interior chamber. A club head member is coupled to the lower end of the shaft housing and defines an open space. A battery is situated in one of the club head member and the shaft housing. An input member is coupled to an outer surface of the shaft housing and electrically connected to the battery, the input member being configured to receive club selection data.

An electronics module having an angular sensing sensor is situated in the club head member. A bend variability assembly is included in the shaft housing for selectively altering a "feel characteristic" of the shaft housing during a swing motion. Alternatively, the shaft housing may actually be length adjustable based on club selection input. A vibration member is positioned in the shaft housing and actuated to simulate a ball impact when the shaft housing is indicative of a swing. A mass variability assembly may be electrically connected to the input member and includes a weight member situated in the shaft housing that is selectively movable therein according to the club selection data so as to simulate club size selections.

It is understood that the technology presented herein may include a software development module or kit that will be integrated into existing and future electronic gaming systems.

Therefore, a general object of this invention is to provide a golf club simulation apparatus that combines the experience of swinging a real golf club with the enjoyment of a video game that simulates a round of golf.

Another object of this invention is to provide a golf club simulation apparatus, as aforesaid, that provides a fixed length (or limited selective length) golf club having structures that selectively change the weight distribution, shaft flexibility, and required shaft angular orientation so as to simulate swinging a selected golf club.

Still another object of this invention is to provide a golf club simulation apparatus, as aforesaid, in which the golf club simulates an impact with a golf ball when making a golf swing of the club, such as with haptic elements such as vibrations and sound.

Yet another object of this invention is to provide a golf club simulation apparatus, as aforesaid, that enables a user to select a desired club audibly or manually.

A further object of this invention is to provide a golf club simulation apparatus, as aforesaid, in which the golf club includes a bend variability assembly that simulates the normal bending of a selected golf club shaft when swinging a golf club.

A still further object of this invention is to provide a golf club simulation apparatus, as aforesaid, having angle and speed sensors configured to collect data on an actual swing of the golf club.

A particular object of this invention is to provide a golf club simulation apparatus, as aforesaid, having electronic components for determining an angular position of the golf shaft housing prior to a swing of the simulation golf club and means for audibly or visually indicating a swing may commence.

Other objects and advantages of the present invention will become apparent from the following description taken in connection with the accompanying drawings, wherein is set forth by way of illustration and example, embodiments of this invention.

BRIEF DESCRIPTION OF THE DRAWINGS

FIG. 1a is a front perspective view of a golf club simulation apparatus according to a preferred embodiment of the present invention;

FIG. 1b is an isolated view on an enlarged scale taken from FIG. 1a;

FIG. 2a is a rear perspective view of the golf club simulation apparatus as in FIG. 1a;

FIG. 2b is an isolated view on an enlarged scale taken from FIG. 2a;

FIG. 3a is a top view of the golf club simulation apparatus as in FIG. 1a;

FIG. 3b is a sectional view taken along line 3b-3b of FIG. 3a;

FIG. 7 is a front perspective view of a golf club simulation apparatus according to another embodiment of the present invention;

FIG. 8a is a front view of the golf club simulation apparatus as in FIG. 7;

FIG. 8b is a sectional view taken along line 8b-8b of FIG. 8a.

FIG. 11 is an exploded view of the golf club apparatus shown in FIG. 9;

DESCRIPTION OF THE PREFERRED EMBODIMENT

Figure 3A:
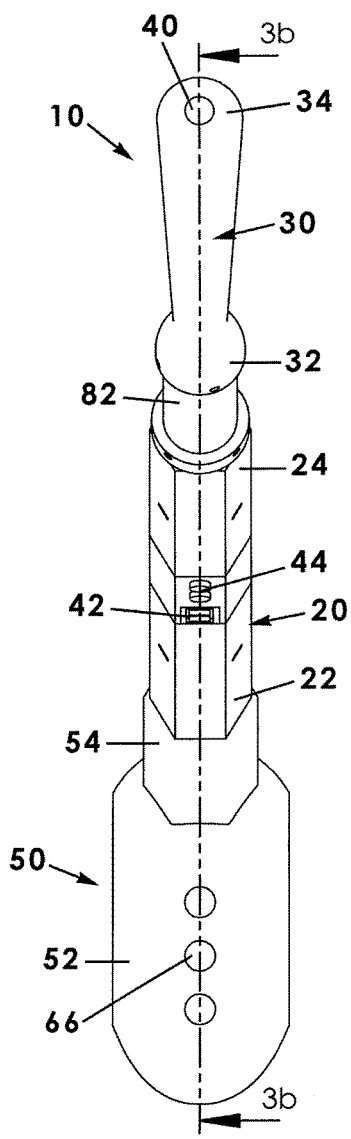

A golf club simulation apparatus according to a preferred embodiment of the present invention will now be described in detail with reference to FIGS. 1 to 14 of the accompanying drawings. The golf club simulation apparatus 10 includes a shaft housing 20, a grip member 30, a club head member 50, a bend variability assembly 80, and a mass variability assembly 90. It is understood that the shaft housing 20, grip member 30, club head member 50, and other related structural components will preferably have symmetrical configurations that may be used equally efficiently by either left or right handed users.

The elongate shaft housing 20 includes opposed lower 22 and upper 24 ends. The shaft housing 20 defines an interior area between upper and lower ends such that other assemblies and electronics may be positioned therein as will be described later. The shaft housing 20 may also include a channel 26 coupled to an outer surface of the shaft housing 20 and extending longitudinally, the channel 26 being configured to receive wires electrically connecting respective electronic components, battery 62, and respective motors. In other embodiments, electrical communications may be with wireless technology. Preferably, the battery 62 is a rechargeable, six-hour battery.

The grip member 30 includes a proximal end 32 operatively coupled to the upper end 24 of the shaft housing 20 and a distal end 34 opposite the proximal end 32. The grip member 30 defines an interior chamber 36 configured to receive other components as will be described later. The grip member 30 may include a construction substantially similar to a grip of a traditional golf club in its appearance and tactile characteristics.

In an embodiment, the golf club simulation apparatus 10 includes a microphone 40 that is positioned within the interior chamber 36 of the grip member 30. Preferably, the microphone 40 is coupled to the distal end 34 of the grip member 30 and is partially situated inside the interior chamber 36 and partially extends from the distal end 34 or is otherwise in communication with the distal end 34, such as through an aperture defined by the distal end (FIG. 1a).

The microphone 40 is at least electrically connected to a digital display 42 positioned along the shaft housing 20 or to associated circuitry or processor. In operation, the microphone 40 is configured to receive audible club selection input data from a user and to translate the input data to the display 42. It is understood that voice recognition software or circuitry may be included as well in order to accurately translate a user's voice command to a meaningful club size indicator to be published by the display 42. Determining a user's club selection is also critical in order to actuate changes in mass variation, shaft bend variation, and the like as will be described later. In one embodiment, a speaker may be also be positioned in the interior chamber 36 and electrically connected to the microphone 40 so as to audibly confirm the audibly spoken club request or a club requested through input buttons 44.

In an embodiment, the display is an LED display 42 coupled to an outer surface of the shaft housing 20 and configured to display one or alphanumeric characters indicative of a currently chosen golf club that is being simulated (FIG. 1b). The display 42 may be electrically connected to the microphone 40 as described above and to any related circuitry that is involved in converting audible speech into an alphanumeric character indicative of a chosen club. The microphone 40 and display 42 may be connected with wires or, in some embodiments, wirelessly. In one embodiment, one or more input button 44 may be positioned adjacent to the display 42 and electrically coupled thereto. A user may then manually enter the number of a golf club to be simulated or may scroll through a list of choices and then select a club identifier.

Figure 9:
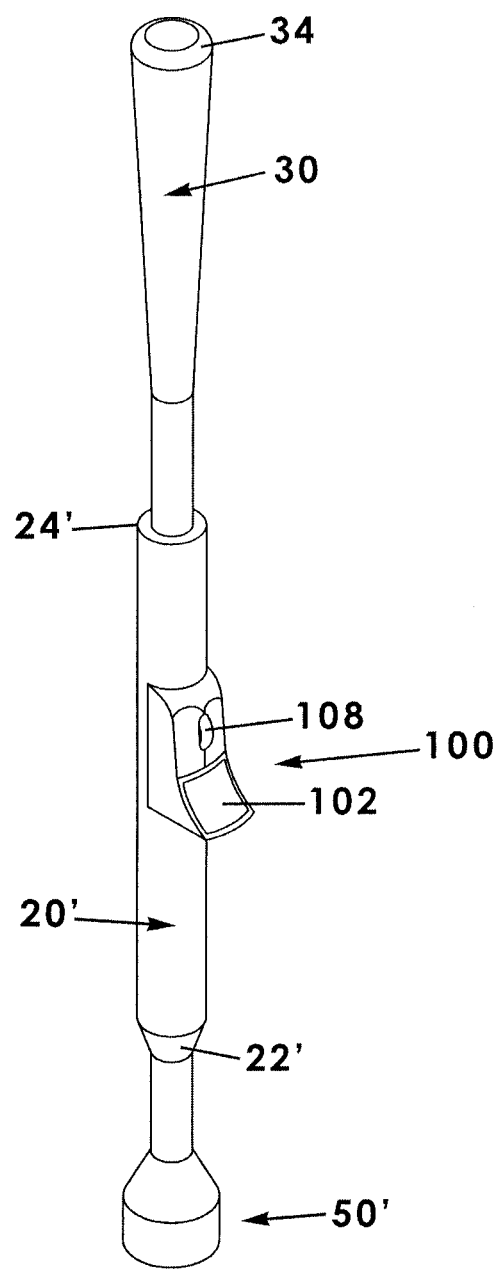
FIG. 9 is a perspective view of a golf club simulation apparatus according to another embodiment of the present invention.
Figure 14:
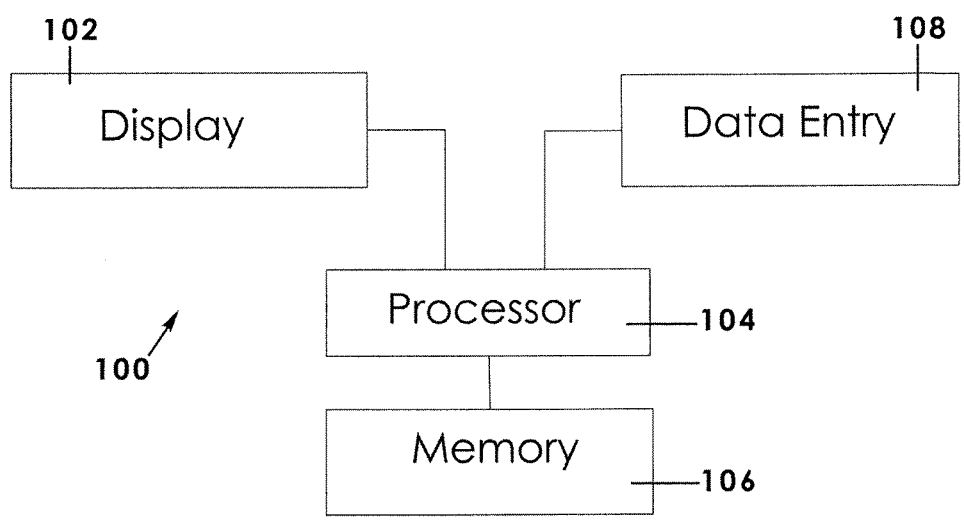
FIG. 14 is a block diagram of the components of an input member.
Figure 15:
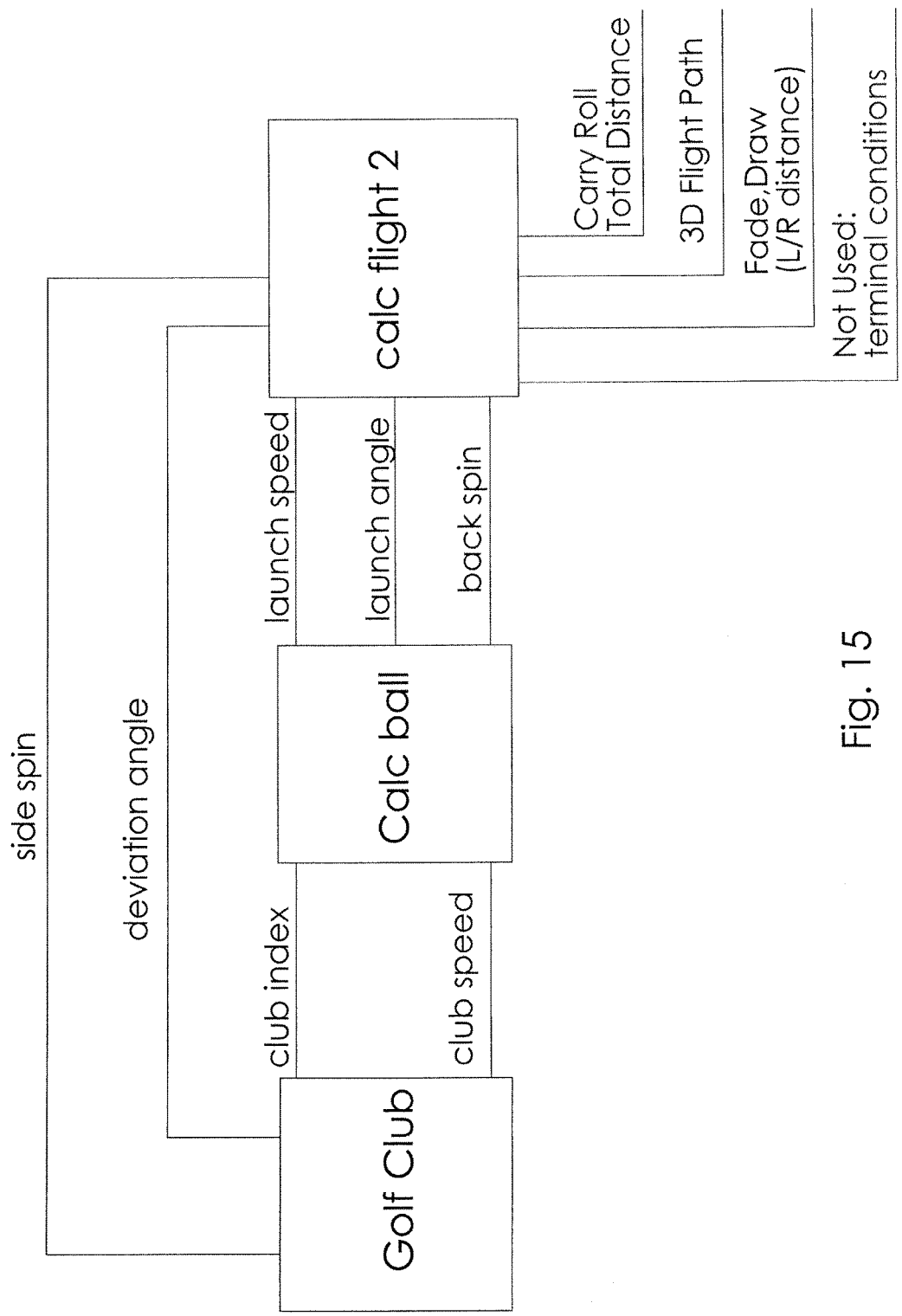
FIG. 15 is a schematic diagram of electronics for processing sensor data.

In another embodiment, a multi-functional input member 100 may be coupled to an outer surface of the shaft housing 20' (FIG. 9). The input member 100 includes a digital display 102 on which may be displayed a club selection, a trajectory of a ball strike, club options, and the like. Further and as shown in FIG. 14, the input member 100 may include a data entry component 108 such as one or more buttons, a keypad, touch screen elements, a dial, or the like, with which club selections may be made by a user. The input member 100 may include circuitry or, preferably, a processor 104 that executes programming instructions stored in a non-volatile memory 106, the processor 104 and memory 106 being situated in the input member 100. The processor 104 may be coupled to the digital display 102 and, executing programming, provide a graphic user interface that enables a user to enter club selection data using the data entry component 108.

In an embodiment, the club head member 50 is coupled to the lower end 22 of the shaft housing 20 and is configured in the manner of a real golf club head. More particularly, the club head member 50 includes an upper portion 54 coupled to the lower end 22 of the shaft housing 20 and a lower portion 52 depending from the upper portion 54 and extending outwardly and perpendicular to an imaginary longitudinal axis defined by the shaft housing 20. The upper portion 54 may be configured to slide over the lower end 22 of the shaft housing 20 and be pinned thereto. The lower portion 52 of the club head member 50 defines an open space in which various electronics and components may be situated.

Figure 3B:
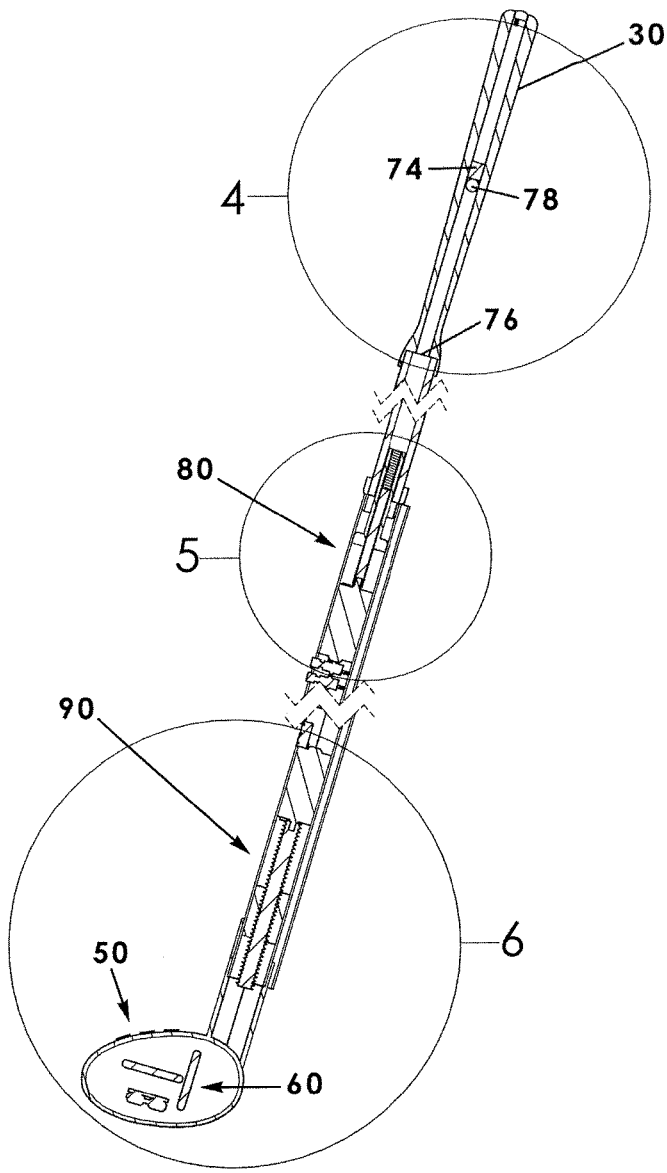
Figure 8B:
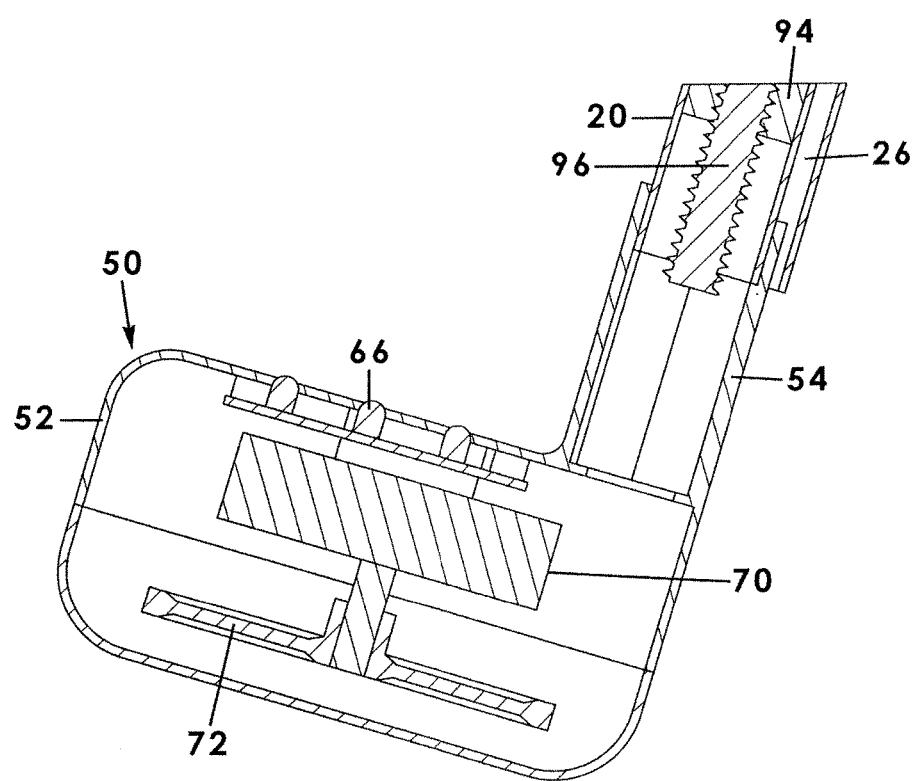

In an embodiment, an electronics module 60 is situated in the lower portion 52 of the club head member 50 and may be electrically connected to the battery 62 (FIG. 3b). Shown in other drawings, the electronics module 60 includes components configured to determine the angle of the shaft housing 20 and of a ball position so as to then indicate when a user may properly swing the club. In one embodiment, the some components of the electronics module 60 may be positioned in the interior chamber 36 of the grip member 30. Positioning some or all of the electronics in the grip member 30 may provide more space in the interior chamber 36 for other components as described below such as a DC motor 70 and flywheel 72 (FIG. 8b).

In this embodiment, the electronics module 60 includes four main components: 1) a gyroscope/accelerometer 64 for collecting club swing data ("angular sensing member"); 2) one or more light emitting diodes 66 ("LEDs") electrically connected to the angular sensing member and configured to be energized when predetermined shaft angle data is indicated by the angular sensing member associated with a current club selection; 3) a battery 62; and 4) ball placement identification components. It is understood that the electronics module 60 is also connected to the display 42 or digital display 102 or other circuitry associated with the means for selecting a club as described above. It is understood that the accelerometer and other electronics may be integrated onto a single circuit board 69.

The accelerometer or gyroscope is configured to analyze many parameters in real time when the club is swinging, such as, but not limited to, swing speed, angular velocity, the weight variation settings (to be described later), air resistance/drag for a selected club, or the like. In addition, a gyroscope is capable of determining the initial (at rest) spatial position of the shaft housing 20 and, only when in a correct position, will actuate respective LEDs to illuminate so as to indicate the club is ready to swing. In an alternative embodiment described later, a proper shaft housing 20 angular position may be displayed as lights or other indicia on a digital display 102 rather than by LEDs 66.

Using triangulation techniques and calculations, the distance between the club head member 50 and a reflective "ball" or start position may be determined and, if the calculations so indicate, the LEDs 66 or digital display 102 may be actuated as an indicator that the club is ready to be swung. For example, a proper start angle can be indicated by lighting a green light, whereas an angle that is too high can be indicated by a blue light and an angle that is too low can be indicated by a red light. It is understood that sound output can also be utilized for indicating an evaluation of correct or incorrect shaft position.

Figure 6:
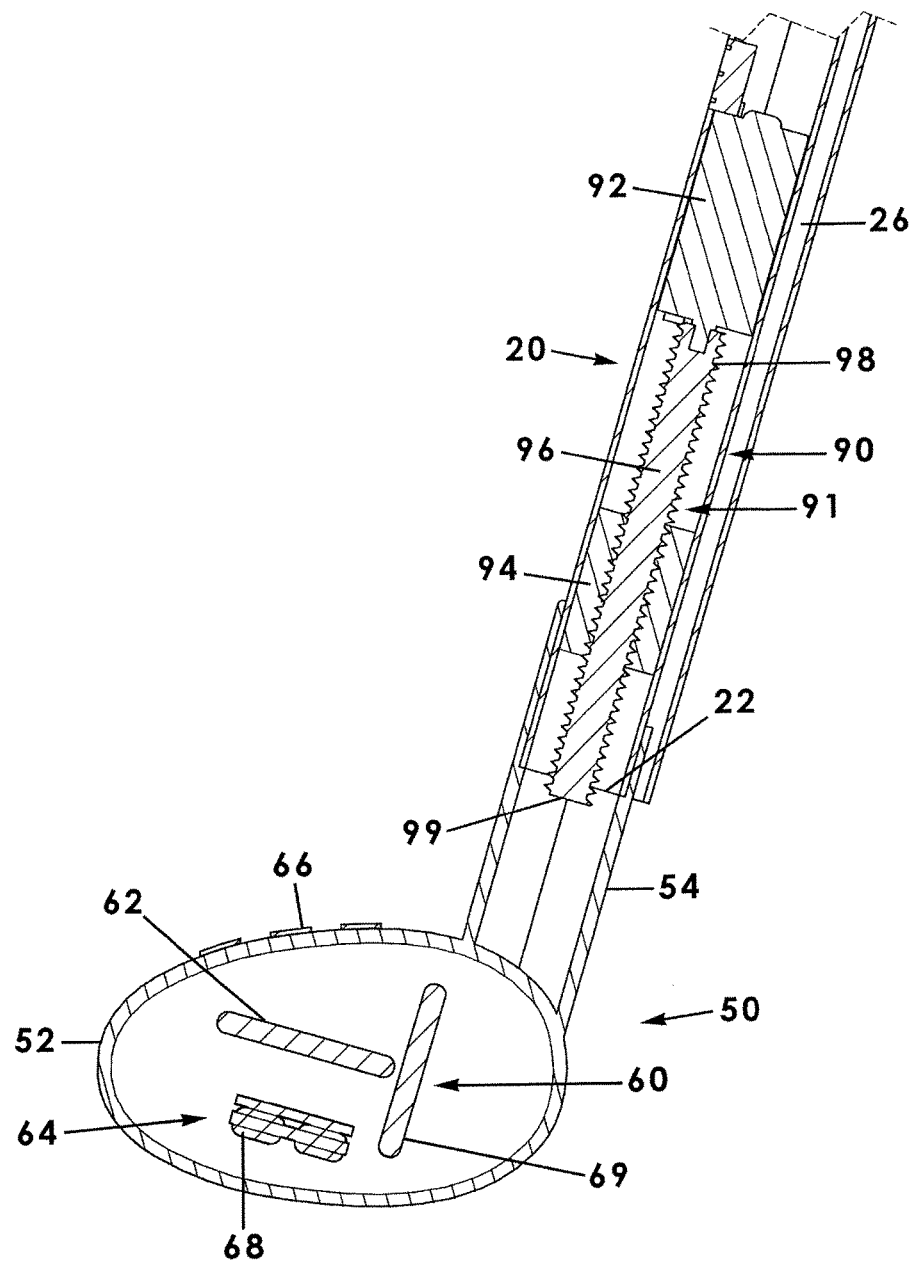
FIG. 6 is an isolated view on an enlarged scale taken from FIG. 3b.

The electronics module 60 may include an ultrasonic sensor 68 configured to determine ball position (FIG. 6). The ultrasonic sensor 68 includes a laser that will make use of a "reflective ball" or, more particularly, will be reflected off of a reflective surface or object to generate a distance by which the circuitry or a processor can determine if the shaft housing 20 is correctly positioned. If so, the LEDs 66 are activated to indicate that the club is ready to swing.

The electronics module may also include sound output electronics. For instance, sound output such as a "swoosh" or a ball impact sound may be output to headphones via a wireless Bluetooth method, the sound output being actuated when movement of the shaft housing 20 is detected and indicative of a swing. The use of sound or vibration effects appeals to a user's senses so as to simulate actual game play. The use of sensory effects is also referred as "haptic" design or simulated perception.

In another embodiment, an image sensor (not shown) with a laser may be used rather than the ultrasonic sensor 68 described above. The image sensor may be configured such that the laser may be turned on and off so that a lens at which the laser is directed can determine a distance the laser is offset from the image frame.

In another embodiment of the club head member 50 (FIGS. 7 to 8b), the lower portion 52 of the club head member 50 includes a circular or disc-shaped configuration in which a gimbaled DC motor 70 with flywheel 72 may be positioned. It is understood that the electronics control circuitry, including battery, is situated above the motor 70 and is electrically connected to the motor 70 and flywheel 72. The flywheel 72 is configured to provide a torque on the shaft housing 20 during a swing according to the principle of conservation of angular momentum. The gimbal (i.e. pivot) allows the angular position (i.e. tilt) of the flywheel 72 relative to the shaft housing 20 to be adjusted either manually or electrically with another motor (not shown). It is understood that the direction and speed of the flywheel 72 affects the magnitude of torque along the shaft housing 20 whereas the tilt of the flywheel 72 affects the orientation of the torque on the shaft housing 20. Further, it is understood that operation of the motor 70 and flywheel orientation may be controlled by the circuitry or a processor in cooperation with the club selection.

In still another embodiment, an alternative club head member 50' may include a generally truncated configuration that defines an interior space dimensioned to hold an electronics module 110. The truncated configuration may have a generally cylindrical, cubical, spherical, ovular, or other three-dimensional shape that defines an interior space. In this embodiment, the electronics module 110 is situated in the interior space and may include a motion sensor 112 configured to detect movement of the club head member 50' and to generate motion data. The electronics module 110 also includes an angular sensing assembly 114 having one or more accelerometers 116 configured to detect a geometric angle of the club head member 50' (and thus of the shaft housing 20) and to generate angle data. Preferably, the accelerometers 116 include a combination of a horizontal accelerometer 116a and a vertical accelerometer 116b that, together, can determine a horizontal and vertical orientation of the club head member 50' and, as a result, an angle of the shaft housing 20. The angular sensing assembly 114 may be referred to as a 3-axis or 6-axis accelerometer. By sensing this angular data, circuitry or programming can determine if the shaft housing 20 is being positioned in a correct or acceptable start position as well determining a swing angle and details regarding how a hypothetical ball is struck and its trajectory. Whether the shaft housing 20 is properly positioned (according to predetermined or pre-programmed data regarding proper shaft angle associated with each size of golf club), an indication of correct position may be indicated visually on the digital display 102 (such as by a cross-hair graphic) or by LEDs 66 as described above.

The motion data from the motion sensor 112 and angle data from the angular sensing assembly 114 may be analyzed by circuitry in the electronics module 110 so as to determine a trajectory of a hypothetical golf ball struck by the club head member 50'. Circuitry in the electronics module 110 may then cause the trajectory data to be graphically displayed on the digital display 102 of the input member 100. In an embodiment, motion data and angle data from respective sensors in the electronics module 110 may be transmitted to the processor 104 in the input member 100 as described previously. The data may be delivered through wires or wirelessly. The processor 104 is electrically connected to the digital display 102 and, executing programming, the trajectory of a virtual ball struck by the club head member as a result of a swing of the shaft housing 20 may be displayed upon the digital display 102. FIG. 14 represents circuitry for processing sensor data, calculating trajectory, and other computations.

In another aspect of the present invention, the bend variability assembly 80 is configured to recognize and simulate that there is a difference in the amount of bend between different types of clubs in a set of traditional golf clubs when swung. In one embodiment, the bend variability assembly 80 operates generally by moving a flexible component inward or outward relative to the shaft housing 20 so as to make more or less of the flexible component available to bend during a swing of the club according to the club selected prior to the swing.

More particularly, the bend variability assembly 80 may include a tubular shaft 82 positioned in the interior area of the shaft housing 20 adjacent the upper end 24 thereof. The tubular shaft 82 is selectively movable, such as by sliding, through the upper end 24 a selected distance into or out of the interior area of the shaft housing 20. The tubular shaft 82 is constructed of a semi-rigid material such as TPE that will bend in a predetermined manner depending on the torque and angular momentum experienced by the shaft housing 20 when the club is swung.

Figure 5:
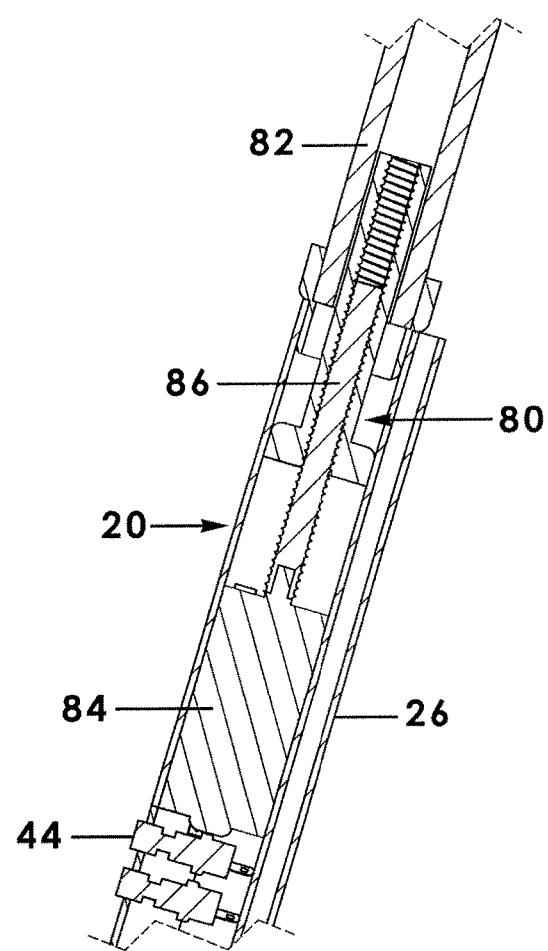
FIG. 5 is an isolated view on an enlarged scale taken from FIG. 3b.

The bend variability assembly 80 further includes a bend shaft motor 84 positioned in the interior area of the shaft housing 20 downwardly adjacent the tubular shaft 82 (FIG. 5). In addition, the bend variability assembly 80 includes a threaded rod 86 having a first end operatively coupled to the tubular shaft 82 and a second end operatively coupled to the bend shaft motor 84. The rod 86 may be threaded and configured to move the tubular shaft 82 into or out of the interior area of the shaft housing 20 depending on the direction of operation of the bend shaft motor 84. The farther the tubular shaft 82 is moved into the interior area of the shaft housing 20, the less of the tubular shaft 82 is available to bend when the club is swung. Conversely, the farther the tubular shaft 82 is moved out of the interior area of the shaft housing 20, the more of the tubular shaft 82 is available to bend when the club is swung. The position of the tubular shaft 82 extended outward/upward of upper end 24 of the shaft housing 20 may be controlled by the circuitry or processor and be predetermined depending on the club selection. It is understood that the inner surface of the shaft housing 20 may define a track along which the tubular shaft 82 is directed.

In another embodiment shown in FIGS. 9 to 12c, a length adjustable bend variability assembly 80' is accomplished in conjunction with a segmented embodiment of the shaft housing 20' (primed numerals being used to identify components that are the same or similar to those described previously). More particularly, the segmented shaft housing 20' includes a lower housing portion 20a (which may also be referred to as an "outer housing") adjacent the lower end 22' of the segmented shaft housing 20'. Further, the segmented shaft housing 20' includes an upper housing portion 20b (which may also be referred to as an "upper housing") adjacent the upper end 24' of the shaft housing 20', the upper housing portion 20b being separate and uncoupled from the lower housing portion 20a (FIG. 10b). The upper housing portion 20b is dimensioned to be selectively and slidably received into the lower housing portion 20a. Specifically, the housing portions are configured such that the upper housing portion 20b is movable between a retracted configuration a selected distance inside the lower housing portion 20a and an extended configuration a selected distance outside the lower housing portion 20a.

Further, the length adjustable bend variability assembly 80' includes a bend linkage 81 configured to move the upper housing portion 20b (and the grip handle 30 attached thereto) between the retracted and extended configurations. The bend linkage 81 of the length adjustable bend variability assembly 80' includes a first end operatively coupled to the bend shaft motor 84' and a second end coupled to the upper housing portion 20b and is configured to move the upper housing portion 20b between respective retracted and extended configurations. The bend shaft motor 84' is electrically connected to the input member 100 such that actuation of the bend shaft motor 84' is according to club selection data. The bend linkage 81 may include a threaded rod coupled to the bend shaft motor 84' and having threads engaged with complementary threads defined by an outer surface of the threaded rod such that the upper housing portion 20b is urged upward or downward depending on a direction in which the bend shaft motor 84' is operated. The threaded rod provides the bend characteristics described previously. It is understood that other linkage assemblies may also be utilized, such as a rack and pinion gear combination, a worm gear, a push-pull arm assembly, a spring assembly, or the like. Preferably, the length of the shaft housing 20' is variable between about 26" to 30". A combination of the bend variability assembly 80 and the bend variability assembly 80' may be used in the present invention. The movement of the upper housing portion 20b between retracted and extended configurations can be seen by comparing FIGS. 10c and 12c, respectively.

Figure 10A:
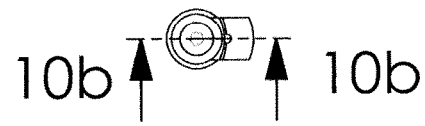
FIG. 10a is a top view of the golf simulation apparatus as in FIG. 9.
Figure 10B:
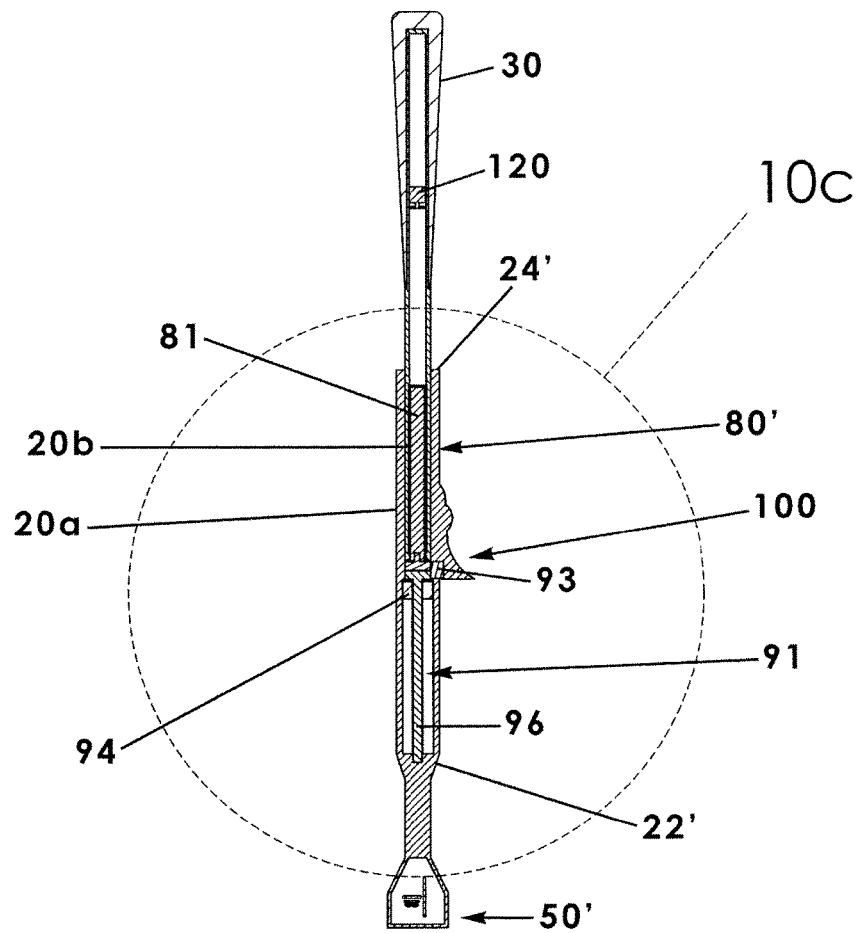
FIG. 10b is a sectional view taken along line 10b-10b of FIG. 10a illustrating bend variability and mass variability assemblies in retracted configurations.
Figure 10C:
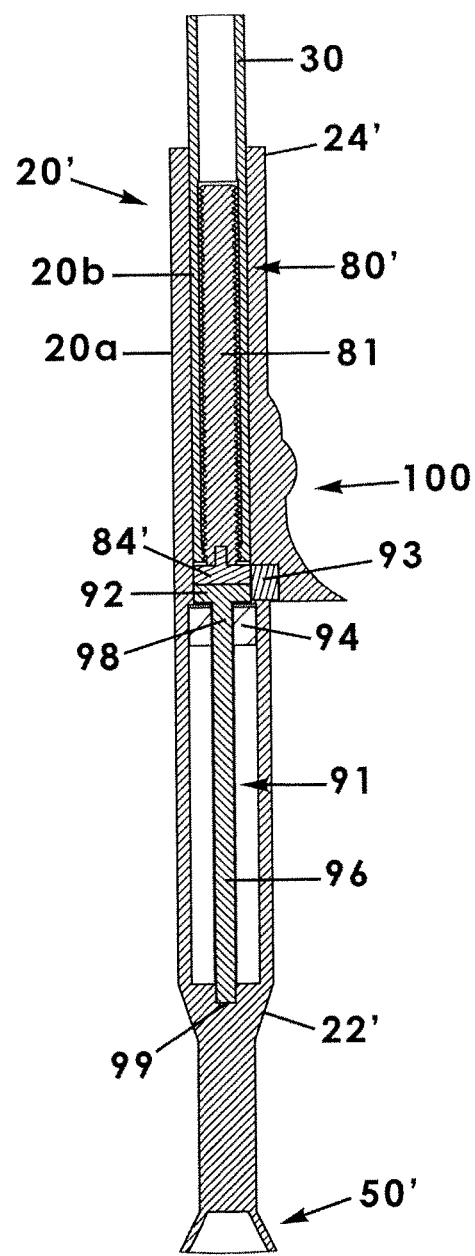
FIG. 10c is an isolated view on an enlarged scale taken from FIG. 10b.
Figure 12A:
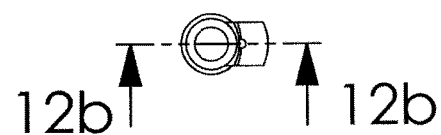
FIG. 12a is a top view of the golf simulation apparatus as in FIG. 9.
Figure 12B:
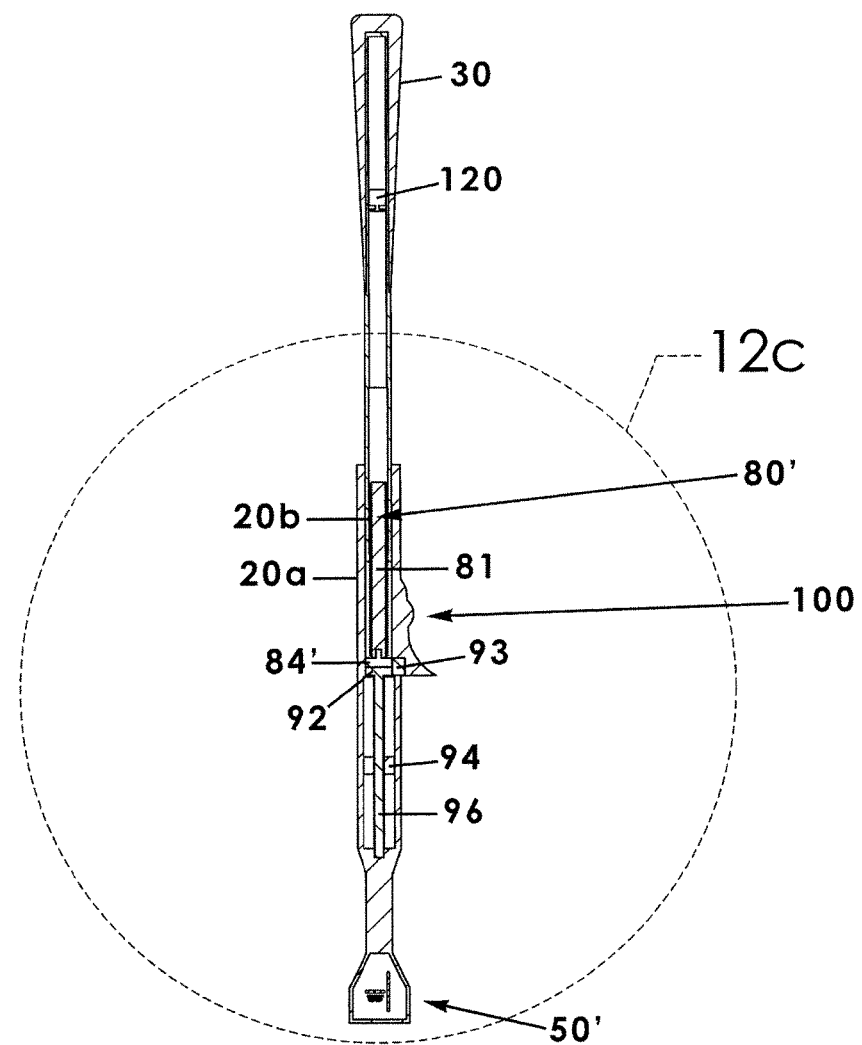
FIG. 12b is a sectional view taken along line 12b-12b of FIG. 12a illustrating bend variability and mass variability assemblies in extended configurations.
Figure 12C:
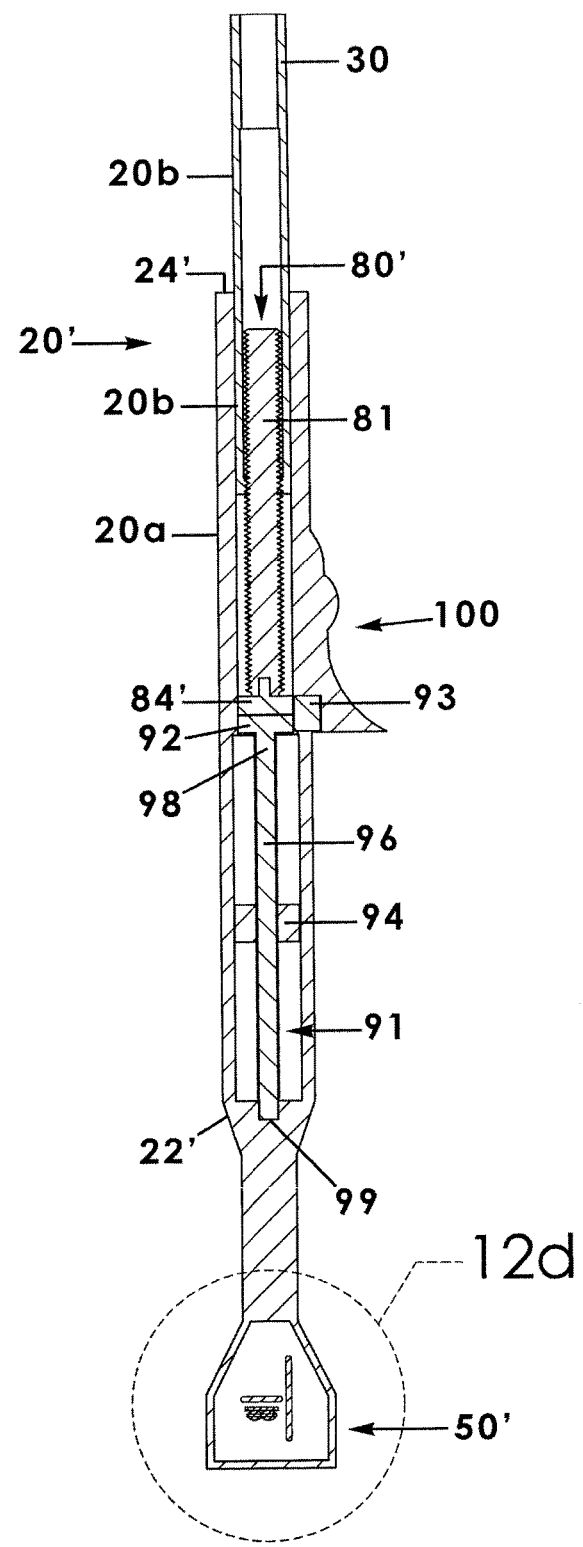
FIG. 12c is an isolated view on an enlarged scale taken from FIG. 12b.
Figure 12D:
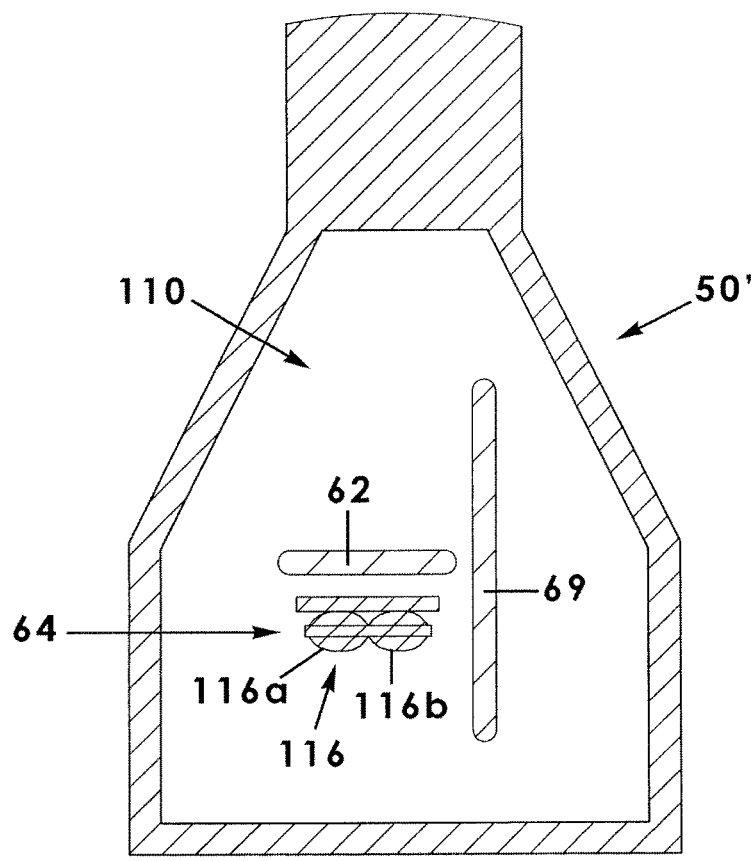
FIG. 12d is an isolated view on an enlarged scale taken from FIG. 12c.
Figure 13:
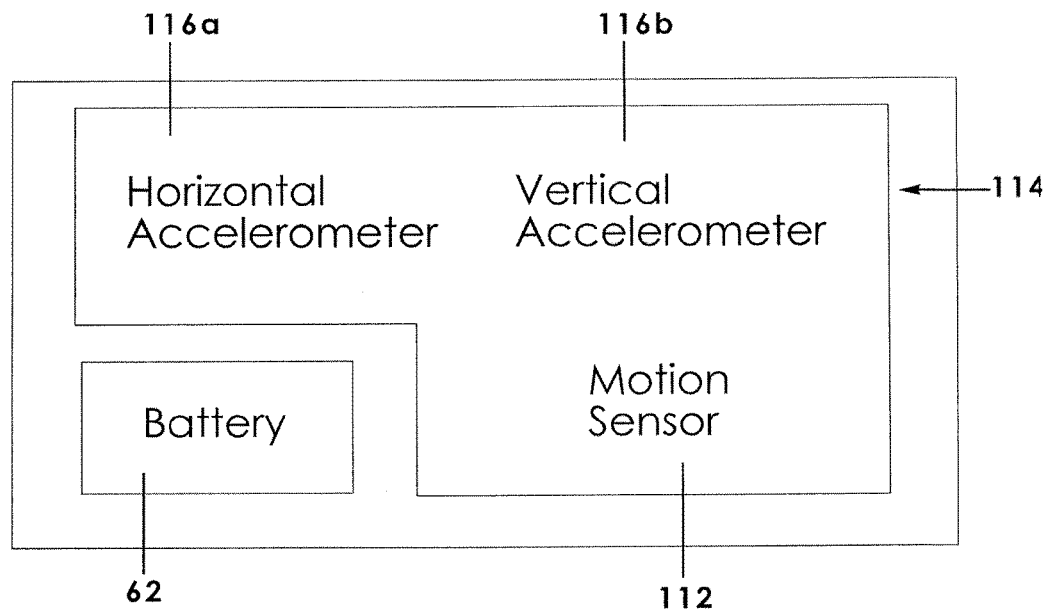
FIG. 13 is a block diagram of an angular sensing assembly.

By way of example, if the club selection data is indicative of a driver, the bend shaft motor 84' may be actuated so as to urge the upper housing portion 20b to move a predetermined distance toward the extended configuration (FIG. 12c)—in other words, to increase the length of the shaft housing 20' as would better simulate swinging a driver (FIG. 11b). Conversely, if the club selection data is indicative of a pitching wedge, the bend shaft motor 84' may be actuated so as to urge the upper housing portion 20b to move a predetermined distance toward the retracted configuration (FIG. 10c)—in other words, to decrease the length of the shaft housing 20' as would better simulate swinging a pitching wedge (FIG. 10b). It is understood that a driver is a much longer club than a pitching wedge and has a different "feel" than that experienced when swinging a shorter club, such as a pitching wedge.

In another aspect of the invention (FIG. 6), the mass variability assembly 90 includes a mass variation motor 92 positioned in the interior area of the shaft housing 20. A weight member 94 is also positioned in the interior area. The mass variability assembly 90 includes a mass linkage 91 configured to selectively move the weight member 94 up and down within the shaft housing 20 so as to change the "feel" of swinging the shaft housing 20 as will be described below. The mass linkage 91 (FIG. 10b) includes a threaded rod 96 having a first end 98 coupled to the mass variation motor 92 and a second end 99 extending downwardly toward the club head member 50 and away from the mass variation motor 92. The weight member 94 may include threads complementary to the threads of the threaded rod 96 such that the weight member 94 travels up or down along the threaded rod 96 when the mass variation motor 92 is actuated, depending on the direction the mass variation motor 92 is operating.

The mass variation motor 92 is electrically connected to the input member 100 (FIGS. 10c and 10c) such that actuation of the mass variation motor 92 is according to club selection data. The input member 100 is configured to actuate the mass variation motor 92 to move the weight member 94 up or down to best simulate a club selection. For example, if the club selection data is indicative of a driver, the mass variation motor 92 may be actuated so as to urge the weight member 94 to move down the threaded rod 96 away from the mass variation motor 92 and toward the club head member 50 (FIG. 6). It is understood that by moving the weight toward the club head member 50, the shaft housing 20 will feel more realistic since a driver is a longer club and heavier at the club end. Conversely, if the club selection data is indicative of pitching wedge, the mass variation motor 92 may be actuated to urge the weight member 94 to move upwardly along the threaded rod 96 toward the mass variation motor 92 and away from the club head member 50. It is understood that by moving the weight upwardly, the shaft housing 20 will feel more realistic since a pitching wedge is a shorter club and not as heavy at the club head end.

Although the mass variation motor 92 and bend shaft motor 84' have been described above as independent components, it is understood in some embodiments, a single motor 93 can be used. For instance, a single motor 93 may be electrically connected to the input member 100 and operatively coupled to the bend linkage 81 and to the mass linkage 91. In the drawings (such as in FIGS. 10b 10c), and 11b), reference numerals 84' and 92 may be seen that a single motor includes two operative portions 84 and 92 (such as gear assemblies) coupled to respective linkages 81 and 91, respectively.

In another aspect, the golf club simulation apparatus 10 also includes a structure for simulating a golf club head striking a golf ball. Again, the invention uses so-called "haptic" means for simulating desired sensory perceptions of swinging an actual golf club. More particularly, a vibrator 120 is positioned proximate the upper end 22' of the shaft housing 20' and in electrical communication with the electronics module 60. Preferably, the vibrator 120 is situated in the interior chamber defined by the grip member 30 although being positioned within the interior area defined by the shaft housing 20' would also work due to its proximity to the grip member 30. The vibrator 120 is activated to vibrate for a predetermined period of time when the shaft housing 20' is detected to return to its start position, i.e. when the club head member 50' swings adjacent the ground/floor where a literal golf ball would be contacted. As described above, the movement and position of the shaft housing 20' are determined by the motion sensor 112 and angular sensing assembly 114, respectively, the angular sensing assembly 114 including one or more accelerometers 116. It is important to detect both motion and position so as to confirm that the club is being swung and not just resting in a start position. In use, the motion sensor 112 is configured to detect when a user is currently swinging the shaft housing 20' and the sensing assembly 114 is configured to indicate when the angle of the club head member 50' is at a start position where a golf ball would be struck. In such case, the vibration simulates an actual ball strike. When the conditions described above are indicated, the circuitry of the electronics module generate and deliver a vibration signal which, when received by the vibrator, actuates the vibrator 120.

Figures 4A, 4B, 4C:
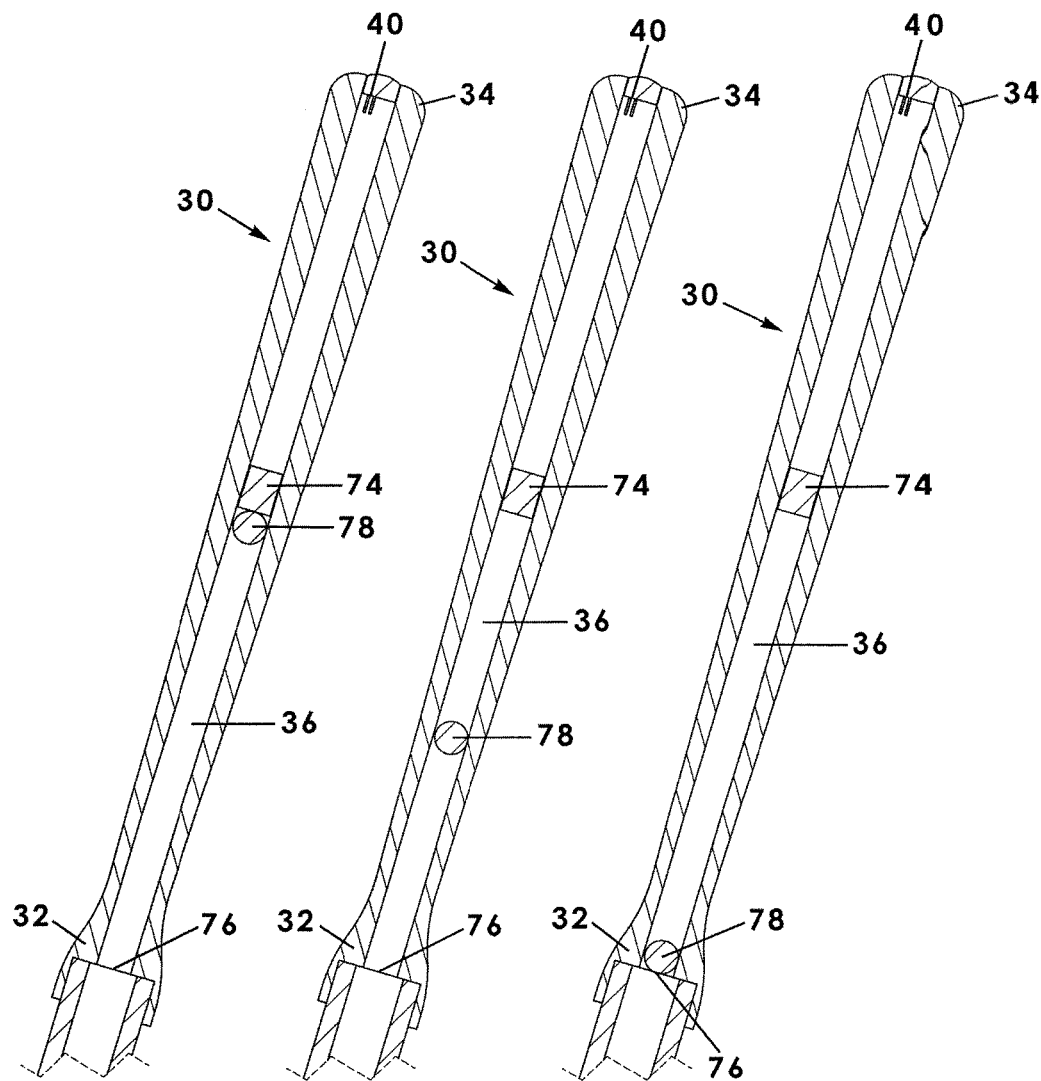
FIG. 4a is an isolated view on an enlarged scale taken from FIG. 3b illustrating a mass fluctuation assembly in a ready configuration.
FIG. 4b is an isolated view on an enlarged scale taken from FIG. 3b illustrating a mass fluctuation assembly in partially swinging configuration.
FIG. 4c is an isolated view on an enlarged scale taken from FIG. 3b illustrating a mass fluctuation assembly in a full swing configuration.

In another embodiment, the means for simulating the club head member 50 striking a golf ball may include a magnet 74 is fixedly coupled and positioned in the interior chamber 36 of the grip member 30 (FIGS. 4a to 4c). Preferably, the magnet 74 is situated about midway between the upper 24 and lower 22 ends of the grip member 30. A stop 76, such as a metal plate is positioned in the interior chamber 36 adjacent the lower end 22 and is displaced from the magnet 74. A ball 78 constructed of either metal or a magnetic material that is complementary to the magnet 74 is also situated in the interior chamber 36. The magnet 74 may be a rare Earth magnet. In use, the ball 78 is magnetically coupled to the magnet 74 when the shaft housing 20 is completely stationary (FIG. 4a) but overcomes the magnetic attraction and is released from the magnet 74 when subjected to the rotational forces of a swing of the club (FIG. 4b). Sufficient rotational forces during a swing cause the ball 78 to impact the stop 76 so as to simulate an impact of the club face of a golf club with a golf ball. It is understood that the impact between ball 78 and stop 76 may produce both an audible and vibratory indication of impact.

In use, a user may decide what size or type of golf club he wants to swing and, therefore, simulated by the golf club simulation apparatus 10. The club choice is selected by the user speaking a numeric or alphanumeric designation into the microphone 30 or by pressing a respective input button 44. The club selection is then "published" on the digital display 42 and may be communicated to other components as described above. The club selection is automatically communicated to the bend variability assembly 80 and mass variability assembly 90 through wires and circuitry or to a processor that is electrically connected to said assemblies. Accordingly, the bend shaft motor 84 is energized to move the tubular shaft 82 of the bend variability assembly 80 to a predetermined position associated with the club selection. Similarly, the mass variability motor 92 is energized to move the weight member 94 to a predetermined configuration associated with the club selection.

The user may then grasp the grip member 30 and prepare to swing the club in a manner similar to swinging a real golf club. Before swinging, however, the angle of the shaft housing 20 must be properly angled and the club head 50 appropriately positioned relative to a simulated ball. Electronics such as the gyroscope 64 may be used to determine angular data regarding the position of the shaft housing 20. Similarly, the ultrasonic sensor 68 or accelerometers 116 may be used to determine if the club head face is properly positioned. When the circuitry or processor determines, with use of data from the angle sensing assembly 114 that the shaft angle and club head face are properly positioned, the LEDs 66 are energized or images published to the digital display 102 to communicate to a user that the shaft housing 20 is ready to swing. Then, when the user swings the apparatus 10, accelerometers and other sensors may collect swing data or statistics. In addition, the torque of the swing causes the ball 78 to be released from the magnet 74 and to strike the stop 76 to simulate a golf club head impacting a golf ball. It is understood that swinging the apparatus 10—having been adjusted to simulate the weight distributions and shaft bend characteristics of a respective club— provides an experience to the user very similar to swinging an associated real golf club.

It is understood that while certain forms of this invention have been illustrated and described, it is not limited thereto except insofar as such limitations are included in the following claims and allowable functional equivalents thereof.

The invention claimed is:

1. A golf club simulation apparatus, comprising:
a shaft housing having opposed lower and upper ends and defining an interior area there between;
a club head member coupled to said lower end of said shaft housing and defining an open space;
a battery situated in one of said club head member and said shaft housing;
an input member coupled to an outer surface of said shaft housing and electrically connected to said battery, said input member being configured to receive club selection data; and
a bend variability assembly electrically connected to said input member and including a tubular bend shaft positioned in said interior area of said shaft housing adjacent said upper end thereof and selectively movable through said upper end toward a retracted configuration inside said interior area and toward an extended configuration outside of said interior area, said bend variability assembly including a bend linkage having a threaded rod having a first end operatively coupled to a bend shaft motor and a second end coupled to said tubular bend shaft and configured to selectively move said tubular bend shaft linearly into or out of said shaft housing upon actuation of said bend shaft motor
wherein said bend shaft is constructed of a semi-rigid material that will bend in a predetermined manner depending on the torque and angular momentum experienced by the shaft housing;
wherein said bend shaft is more flexible proportionate to a distance said bend shaft is extended out of said shaft housing.

2. The golf simulation apparatus as in claim 1, further comprising:
a mass variability assembly electrically connected to said input member and having a weight member situated in said shaft housing that is selectively movable therein according to said club selection data;
wherein said mass variability assembly includes:
a mass variation motor positioned in said interior area of said shaft housing that is electrically connected to said battery and to said input member;
a mass linkage including a threaded rod having a first end operatively coupled to said mass variation motor and a second end extending away from said mass variation motor, said weight member being operatively coupled to said threaded rod and configured to selectively move up or down along said threaded rod when said mass variation motor is actuated selectively according to said club selection data and only prior to a golf swing.

3. The golf club simulation apparatus as in claim 1, comprising:
an electronics module positioned in said open space of said club head member and electrically connected to said battery;
wherein said electronics module includes:
a motion sensor configured to detect movement of said club head member, said motion sensor generating motion data;
an angular sensing assembly configured to detect a geometric angle of said shaft housing, said angular sensing assembly generating angle data;
a vibrator positioned proximate said upper end of said shaft housing and configured in wireless communication with said electronics module;
wherein said motion sensor and said angular sensing assembly are configured to generate a vibration activation signal when said motion data and said angle data are indicative that said shaft housing is in motion and that said club head member is proximate a ground surface; and
wherein said vibrator is actuated upon receiving said vibration activation signal.

4. The golf simulation apparatus as in claim 1, comprising a grip member having a proximal end operatively coupled to said upper end of said shaft housing and a distal end displaced from said proximal end, said grip member defining an interior chamber.

5. The golf simulation apparatus as in claim 4, comprising:
- a magnet positioned in said interior chamber of said grip member;
- a stop plate situated in said chamber and displaced downwardly from said magnet;
- a ball having a metallic or magnetic construction that is movable between a start configuration normally magnetically coupled to said magnet and a deployed configuration coupled to said stop plate when said shaft housing is rotated with a predetermined amount of force.

6. The golf simulation apparatus as in claim 1, comprising:
- an electronics module positioned in said open space of said club head member and electrically connected to said battery;
- wherein said electronics module includes:
    - a motion sensor configured to detect movement of said club head member, said motion sensor generating motion data; and
    - an angular sensing assembly configured to detect a geometric angle of said shaft housing, said angular sensing assembly generating angle data.

7. The golf simulation apparatus as in claim 6, comprising:
- a vibrator positioned proximate said upper end of said shaft housing and configured in wireless communication with said electronics module;
- wherein said motion sensor and said angular sensing assembly are configured to generate a vibration activation signal when said motion data and said angle data are indicative that said shaft housing is in motion and that said club head member is proximate a ground surface; and
- wherein said vibrator is actuated upon receiving said vibration activation signal.

8. The golf simulation apparatus as in claim 7, comprising a grip member having a proximal end operatively coupled to said upper end of said shaft housing and a distal end displaced from said proximal end, said grip member defining an interior chamber;
- wherein said vibrator is positioned in said interior chamber of said grip member.

9. The golf simulation apparatus as in claim 6, wherein said angular sensing assembly includes a pair of accelerometers that are configured to determine an angle of said shaft housing.

10. The golf simulation apparatus as in claim 9, comprising circuitry in said electronics module configured to determine from said motion data and said angle data a trajectory of a hypothetical golf ball impacted upon an actual swing of said shaft.

11. The golf simulation apparatus as in claim 9, wherein said pair of accelerometers includes a horizontal accelerometer and a vertical accelerometer.

12. The golf club simulation apparatus as in claim 6, wherein said input member includes:
- a digital display configured to provide a graphic user interface;
- a data entry component configured to receive data from a user;
- a memory configured to store entered data, predetermined golf club data, and programming instructions;
- a processor in data communication with said memory configured to execute said programming instructions.

13. The golf club simulation apparatus as in claim 12, comprising:
- programming in said memory that, when executed by said processor, causes said processor to determine from said motion data and said angle data a trajectory of a hypothetical golf ball impacted upon an actual swing of said shaft;
- programming in said memory that, when executed by said processor, causes said processor to publish data indicative of said determined trajectory to said digital display.

14. The golf club simulation apparatus as in claim 12, wherein:
- said angular sensing assembly includes a pair of accelerometers that are configured to determine an angle of said shaft housing;
- said golf club simulation apparatus further comprising:
- programming in said memory that, when executed by said processor, causes said processor to determine, via said pair of accelerometers, if said angle of said shaft housing matches a predetermined angle associated with said club selection data and, if so, to publish an affirmative indicia to said digital display.

15. The golf club simulation apparatus as in claim 1, wherein said input member includes:
- a digital display configured to provide a graphic user interface;
- a data entry component configured to receive data from a user;
- a memory configured to store entered data, predetermined golf club data, and programming instructions; and
- a processor in data communication with said memory configured to execute said programming instructions.

16. The golf club simulation apparatus as in claim 15, comprising programming in said memory that, when executed by said processor, causes said processor to publish digital data indicative of a swing of said shaft housing to said digital display.

17. The golf club simulation apparatus as in claim 15, wherein:
- said data entry component includes a microphone configured to receive audible data from a user, said microphone being in data communication with said processor;
- programming in said memory that, when executed by said processor, causes said processor to convert said audible data into club selection data and to publish said club selection data to said digital display.

18. A golf club simulation apparatus, comprising:
- a shaft housing having opposed lower and upper ends and defining an interior area there between;
- a club head member coupled to said lower end of said shaft housing and defining an open space;
- a battery situated in one of said club head member and said shaft housing;
- an input member coupled to an outer surface of said shaft housing and electrically connected to said battery, said input member being configured to receive club selection data;
- a bend variability assembly electrically connected to said input member and including a bend linkage situated in said interior area of said shaft housing that is operably coupled to said motor, said linkage being selectively movable linearly when said motor is actuated;

a mass variability assembly electrically connected to said input member and having a weight member situated in said shaft housing that is selectively movable therein according to said club selection data;

wherein said mass variability assembly includes:

a mass variation motor different from said bend shaft motor positioned in said interior area of said shaft housing that is electrically connected to said battery and to said input member; and a mass linkage including a threaded rod having a first end operatively coupled to said mass variation motor and a second end extending away from said mass variation motor, said weight member being operatively coupled to said threaded rod and configured to selectively move up or down along said threaded rod when said mass variation motor is actuated selectively according to said club selection data and only prior to a golf swing.

* * * * *